United States Patent
Kim et al.

(10) Patent No.: US 11,456,485 B2
(45) Date of Patent: Sep. 27, 2022

(54) SULFONE SULFONYLIMIDE COMBINATIONS FOR ADVANCED BATTERY CHEMISTRIES

(71) Applicant: U.S. Army Combat Capabilities Development Command, Army Research Labortary, Adelphi, MD (US)

(72) Inventors: Judith A. Kim, Oakland, CA (US); Marshall A. Schroeder, Pasadena, MD (US); Arthur von Wald Cresce, Beltsville, MD (US); Kang Xu, Potomac, MD (US); Lin Ma, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 300 days.

(21) Appl. No.: 16/850,121

(22) Filed: Apr. 16, 2020

(65) Prior Publication Data

US 2021/0066754 A1    Mar. 4, 2021

Related U.S. Application Data

(60) Provisional application No. 62/895,623, filed on Sep. 4, 2019.

(51) Int. Cl.
| | | |
|---|---|---|
| *H01M 10/0568* | (2010.01) | |
| *H01M 10/0567* | (2010.01) | |
| *H01M 10/36* | (2010.01) | |
| *H01G 11/52* | (2013.01) | |
| *H01G 11/64* | (2013.01) | |
| *H01G 11/62* | (2013.01) | |
| *C07C 317/04* | (2006.01) | |
| *C07C 311/49* | (2006.01) | |

(52) U.S. Cl.
CPC ....... *H01M 10/0568* (2013.01); *C07C 311/49* (2013.01); *C07C 317/04* (2013.01); *H01G 11/52* (2013.01); *H01G 11/62* (2013.01); *H01G 11/64* (2013.01); *H01M 10/0567* (2013.01); *H01M 10/36* (2013.01); *H01M 2300/0002* (2013.01); *H01M 2300/0025* (2013.01)

(58) Field of Classification Search
CPC ........... H01M 10/0568; H01M 10/056; H01M 10/052; H01M 10/0525; H01M 10/0569; H01G 11/62; H01G 11/64
See application file for complete search history.

(56) References Cited

U.S. PATENT DOCUMENTS

2011/0200848 A1* 8/2011 Chiang .................. H01M 8/20
  429/105
2015/0249244 A1* 9/2015 Thieme ................ H01M 50/411
  429/231.1

OTHER PUBLICATIONS

Alvarado, et al. "A carbonate-free, sulfone-based electrolyte for high-voltage Li-ion batteries". Materials Today. vol. 21, No. 4. May 2018. United States.

* cited by examiner

*Primary Examiner* — Stewart A Fraser
(74) *Attorney, Agent, or Firm* — Emily C. Moscati

(57) ABSTRACT

Disclosed is an electrochemical cell, which may be used for advanced rechargeable batteries. The electrochemical cell comprises two or more electrodes within an electrolyte solution, where the electrolyte solution containing (i) an aliphatic or cyclic sulfone and (ii) a metal perfluoroalkylsulfonylimide salt.

10 Claims, 2 Drawing Sheets

SULFONE SULFONYLIMIDE COMBINATIONS FOR ADVANCED BATTERY CHEMISTRIES

CROSS-REFERENCE TO RELATED APPLICATIONS

This application claims priority benefit to U.S. Provisional Patent Application No. 62/895,623, filed on Sep. 5, 2019, which is incorporated herein by reference in its entirety.

TECHNICAL FIELD

The present invention relates to a non-aqueous electrolyte and its related aqueous hybrid electrolytes that improve the performance of advanced battery chemistries, including Li-ion battery and beyond Li-ion battery that involve conversion-reaction type cathode materials, as well as analogous alkali, alkaline earth, transition metal, and post-transition metal cation chemistries including, but not limited to, sodium, magnesium, zinc, or aluminum ions. More particularly, this invention relates to a new combination of salt and solvent chemistries that can simultaneously form protective interphasial layers on both anode and cathode surfaces, allowing for highly reversible battery operation.

BACKGROUND

Rechargeable batteries that output high cell voltages (>3.0 V) utilize non-aqueous and aprotic solvents to dissolve the conducting salts, because these solvents are able to afford the stability against the oxidative or reductive reactions incurred by electrode surfaces of extreme potentials. Because the electrolyte components are almost never thermodynamically stable on the strongly reductive surfaces of anode or strongly oxidative surfaces of cathode, the electrochemical stability is rather attained through the passivation of the electrode surfaces to protect against propagating parasitic reactions. The above passivation is realized by the initial decompositions of the solvent and salt in trace amount and the subsequent deposition of these decomposition products which deactivate the catalytic decomposition sites of the electrode surfaces. Almost universally in all electrochemical devices that produce cell voltages higher than 3.0 V, and particularly in Li ion battery chemistries, certain solvents were developed in the prior arts so that their decomposition products on anode and cathode surfaces are able to form dense and protective interphasial layers. These solvents include ethylene carbonate (EC), vinylene carbonate (VC) and other polar and aprotic solvents and/or additives, have become the indispensable components in all commercial Li ion batteries.

However, the passivation formed by the above-described solvents, salts and/or additives in state-of-the-art electrolytes meets severe challenges when more chemically aggressive, next generation cathode or anode materials are introduced in order to achieve higher energy and/or power density. Such advanced electrode materials either operate at very destructive potentials (>4.5 V), experience dynamic phase changes during each electrochemical cycle, or involve multiphase reactions. Conventional electrolyte formulations are unable to stabilize these highly reactive interfaces, therefore new electrolyte compositions have to be developed. Certain high-energy-density metal anode electrode materials suffer from irreversible nature issues (e.g. poor Coulombic efficiency, dendrite formation).

Therefore, it is highly desirable to develop a new electrolyte composition that would enable advanced battery chemistries. More specifically, it is highly desirable to identify a new electrolyte system which can form passivation layers on both anode and cathode surfaces that provide robust protection over a wide temperature range but are also sufficiently conductive and allow fast kinetics of the cell chemistry.

BRIEF SUMMARY

A first aspect of the present disclosure is drawn to an electrochemical cell, where the electrochemical cell includes two or more electrodes operably connected to an electrolyte solution, where the electrolyte solution containing (i) an aliphatic or cyclic sulfone and (ii) a metal perfluoroalkylsulfonylimide salt having a total molar mass greater than 200 g/mol.

In certain embodiments, the aliphatic or cyclic sulfone is Tetramethylene sulfone (sulfolane), Trimethylene sulfone (TriMS), 1-Methyltrimethylene sulfone (MTS), Ethylmethyl sulfone (EMS), Ethyl-sec-butyl sulfone (EsBS), Ethyl-iso-butyl sulfone (EiBS), Ethyl-iso-propyl sulfone (EiPS), Trifluoropropylmethyl sulfone (FPMS), Dimethylsulfone, Methanesulfonyl fluoride, or a combination thereof In some embodiments, the electrolyte solution also comprises water.

In certain embodiments, the metal perfluoroalkylsulfonylimide salt comprises Li, Na, Zn, Mg, Ca, or Al. In some embodiments, the metal perfluoroalkylsulfonylimide salt is Lithium bis(trifluoromethane)sulfonimide (LiTFSI), Lithium bis(perfluoroethanesulfonyl)imide (LiBETI), Sodium bis(fluorosulfonyl)imide (NaFSI), Magnesium bis(trifluoromethane)sulfonimide Mg(TFSI)$_2$, Zinc bis(trifluoromethane)sulfonimide Zn(TFSI)$_2$, or combinations thereof. Optionally, the metal perfluoroalkylsulfonylimide salt is present in the electrolyte solution at a concentration of between 0.1M and 10M.

In some embodiments, the electrochemical cell includes at least one separator, each separator positioned at least partially between two of the two or more electrodes. In some embodiments, the separator is a porous polyolefin or glass microfiber separator, a polymer separator that is gellable with the electrolytes, or a ceramic or glass solid electrolyte separator.

In some embodiments, other additives may be included in the electrolyte solution, and may be in the electrolyte solution in an amount of between 0.01% and 10% by weight.

DETAILED DESCRIPTION

As used herein, the term "sulfone" refers to either cyclic or aliphatic organic molecules in which sulfur (S) is double-bonded with two oxygens and two single-bonded with either aliphatic or aromatic radicals;

As used herein, the term "imides" refers to a salt chemistry in which the battery system's charge carrying cation (e.g. lithium) is bonded through coulombic interaction to a N-based anion with one or two aliphatic or aromatic radicals.

As used herein, the term "fluoroalkylsulfonyl imides" refers to a salt chemistry in which the battery system's charge carrying cation (i.e. lithium) is bonded to a N-based anion with one or two aliphatic or aromatic radicals, where the protons on the radicals are partially replaced by fluorines.

As used herein, the term "perfluoroalkylsulfonyl imides" refers to a salt chemistry in which the battery system's charge carrying cation (i.e. lithium) is bonded to a N-based anion with one or two aliphatic or aromatic radicals, where all the protons on the radicals are replaced by fluorines.

As used herein, the term "half cells" refers to a common test platform for characterizing half of an energy storage device in which the electrode of interest is typically coupled to an infinite source of the active cation, such as Li metal for Li-ion systems. "Symmetric cells" are the testing devices in which the cathode and anode couple are the same metal electrodes. Complementarily, "Full cells" are the conventionally considered devices in which the cathode and anode couple are capacity matched and performance of both electrodes strongly dictates device performance.

A first aspect of the present disclosure is drawn to an electrochemical cell. Such cells include but are not limited to, (1) lithium and lithium ion cells that use lithiated transition metal oxides or lithiated olivine metal phosphate as cathode, and lithium metal, lithium alloys, metal oxides or sulfides, carbonaceous materials as anode; (2) dual intercalation cells in which both cation and anion intercalate simultaneously into lattices of anode and cathode materials, respectively; (3) cells that use lithium metal, zinc metal, carbonaceous materials, silicon, tin and various lithium alloys as anode materials, and metal oxides, metal halides, sulfides and sulfur, and oxygen as conversion-reaction type cathode materials; (4) electrochemical double layer capacitors based on various electrode materials of high surface area; (5) supercapacitors, and (6) electrolysis cells that produce chemical species at extreme potentials. Such cells can be assembled according to the procedures are known to those of skill in the art.

Figure 1:
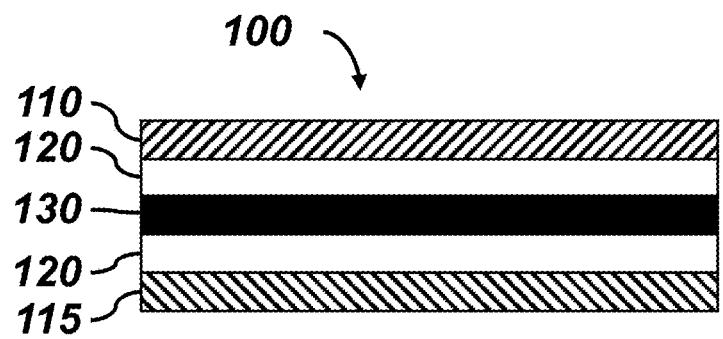
FIG. 1 is a simplified diagram of an electrochemical cell.

The disclosed electrochemical cell can be understood with reference to FIG. 1. As can be seen, the electrochemical cell (100) contains at least two electrodes (110, 115). Typically, one electrode will function as an anode (110) and one as a cathode (115).

In some embodiments, at least one electrode is a negative electrode comprising an active material that is: (a) lithium metal, (b) a lithium alloy with other metals such as silicon or tin, (c) a carbonaceous material with various degree of graphitization, (d) a lithiated metal oxide or chalcogenide, or (e) analogous chemistries for other battery cations (Na, Zn, Mg, Ca, Al).

In some embodiments, at least one electrode is a positive electrode comprising an active material that is (a) a transition metal oxide, (b) a metal halide, (c) a metal phosphate, (d) metal chalcogenides, (e) a carbonaceous material with various degree of graphitization, or (f) sulfur-based cathode materials embedded or confined in various meso-or micropores of carbon hosts.

The electrodes (110, 115) are operably connected to an electrolyte solution (120), and may optionally have at least one separator (130), where each separator is positioned at least partially between two electrodes (110, 115).

The electrolyte solution (120) should contain at least (i) an aliphatic or cyclic sulfone and (ii) a metal perfluoroalkylsulfonylimide salt having a total molar mass greater than 200 g/mol, both of which will be discussed in turn, below.

Aliphatic or Cyclic Sulfone

The aliphatic or cyclic sulfone, by itself or with other compounds, functions as the solvent. In some embodiments, the sulfone has the structure $R-SO_2-R'$, where R and R' are independently: (a) hydrogen, (b) a halogen, or (c) a substituted or unsubstituted straight or branched $C_1-C_6$ alkyl, alkene, or alkynyl. In some embodiments, the sulfone comprises at least one fluorine.

The sulfone is more preferably a sulfone selected from those listed below in Table 1, or a derivative thereof.

TABLE 1

Exemplary Sulfones.

| Chemical Name | CAS# | Structure |
|---|---|---|
| Tetramethylene sulfone (sulfolane) | 126-33-0 | 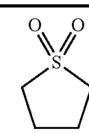 |
| Trimethylene sulfone (TriMS) | 5687-92-3 | 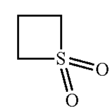 |
| 1-Methyltrimethylene sulfone (MTS) | 24609-83-4 | 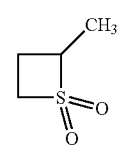 |
| Ethylmethyl sulfone (EMS) | 594-43-4 | 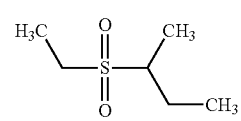 |
| Ethyl-sec-butyl sulfone (EsBS) | (N/A) | 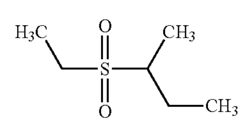 |
| Ethyl-iso-butyl sulfone (EiBS) | 34008-93-0 | 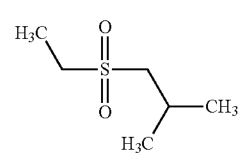 |
| Ethyl-iso-propyl sulfone (EiPS) | 4853-75-2 | 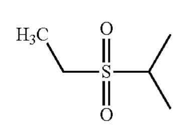 |

TABLE 1-continued

Exemplary Sulfones.

| Chemical Name | CAS# | Structure |
|---|---|---|
| Trifluoropropylmethyl sulfone (FPMS) | 222611-24-7 | H₃C–S(=O)(=O)–CH₂CH₂–CF₃ |
| Dimethylsulfone | 67-71-0 | CH₃–S(=O)(=O)–CH₃ |
| Methanesulfonyl fluoride | 558-25-8 | CH₃–S(=O)(=O)–F |

In some embodiments, one or more sulfones are utilized. Thus, in certain embodiments, the aliphatic or cyclic sulfone is Tetramethylene sulfone (sulfolane), Trimethylene sulfone (TriMS), 1-Methyltrimethylene sulfone (MTS), Ethylmethyl sulfone (EMS), Ethyl-sec-butyl sulfone (EsBS), Ethyl-iso-butyl sulfone (EiBS), Ethyl-iso-propyl sulfone (EiPS), Trifluoropropylmethyl sulfone (FPMS), Dimethylsulfone, Methanesulfonyl fluoride, or any combination thereof In some embodiments, two or more sulfones are used.

In some embodiments, variations of the compounds in Table 1 are utilized. For example, in some embodiments, one or more hydrogen atoms in a compound in Table 1 is replaced with a heteroatom, such as a halogen atom. In some embodiments, e.g., different tail configurations and/or functional groups (e.g., $CF_3$, $CH_3$, etc.) are introduced.

In some embodiments, the aliphatic or cyclic sulfone has a total molecular mass >125 g/mol. In some embodiments, the aliphatic or cyclic sulfone has a total molecular mass <100 g/mol.

Metal Perfluoroalkylsulfonylimide Salt

The electrolyte solutions are prepared by mixing one or more of the perfluoroalkylsulfonylimide salts of the active cation in the electrolytes solution.

The metal perfluoroalkylsulfonylimide salt should have a total molar mass greater than 200 g/mol. In some embodiments, the salt has a total molar mass >250 g/mol. In some embodiments, the salt has a total molar mass >290 g/mol.

The metal perfluoroalkylsulfonylimide salt is preferably a salt selected from those listed below in Table 2, or a derivative thereof.

TABLE 2

Exemplary Perfluoroalkylsulfonylimide Salts.

| Salt Name | CAS # | Structure |
|---|---|---|
| Lithium bis(trifluoromethane)sulfonimide (LiTFSI) | 90076-65-6 | $Li^+$ [(CF₃SO₂)₂N]⁻ |
| Lithium bis(perfluoroethanesulfonyl)imide (LiBETI) | 132843-44-8 | $Li^+$ [(C₂F₅SO₂)₂N]⁻ |
| Sodium bis(fluorosulfonyl)imide (NaFSI) | 100669-96-3 | $Na^+$ [(FSO₂)₂N]⁻ |
| Magnesium bis(trifluoromethane)sulfonimide Mg(TFSI)₂ | 133395-16-1 | $Mg^{2+}$ [(CF₃SO₂)₂N]⁻₂ |

TABLE 2-continued

Exemplary Perfluoroalkylsulfonylimide Salts.

| Salt Name | CAS # | Structure |
|---|---|---|
| Zinc bis(trifluoromethane)sulfonimide Zn(TFSI)$_2$ | 168106-25-0 | 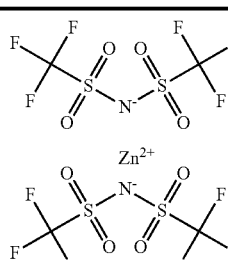 |

In some embodiments, the salts may have the formula M[N(SO$_2$C$_n$F$_{2n+1}$)(SO$_2$C$_m$F$_{2m+1}$)]$^-$$_x$, where M is an alkali metal, alkaline earth metal, transition metal, or post-transition metal, x is 1, 2, or 3, and m+n are ≥1. Preferred alkali metals include Li and Na. Preferred alkaline earth metals include Mg and Ca. Preferred transition metals include Ni, Cu, and Zn. Preferred post-transition metals include Al and Sn. Thus, in certain embodiments, the metal perfluoroalkylsulfonylimide salt may comprise, e.g., Li, Na, Zn, Mg, Ca, or Al. In some embodiments, the metal perfluoroalkylsulfonylimide salt is Lithium bis(trifluoromethane)sulfonimide (LiTFSI), Lithium bis(perfluoroethanesulfonyl)imide (LiBETI), Sodium bis(fluorosulfonyl)imide (NaFSI), Magnesium bis(trifluoromethane)sulfonimide Mg(TFSI)$_2$, Zinc bis(trifluoromethane)sulfonimide Zn(TFSI)$_2$, or combinations thereof.

In some embodiments, variations of the compounds in Table 2 are utilized. For example, in some embodiments, one or more hydrogen atoms in a compound in Table 2 is replaced with a heteroatom, such as a halogen atom.

Optionally, the total metal perfluoroalkylsulfonylimide salt concentration in the electrolyte solution is between 0.1M and 10M.

One or more metal perfluoroalkylsulfonylimide salts may be used. In some embodiments, the only salt present in the electrolyte solution is a single metal perfluoroalkylsulfonylimide salt. In some embodiments, the only salts present in the electrolyte solution are two or more metal perfluoroalkylsulfonylimide salts.

In some embodiments, other additives may be included in the electrolyte solution as known to those of skill in the art. Additives that are envisioned include co-salts, solid electrolyte interface (SEI)-forming agents, cathode protection agents, salt stabilizers, safety protect agents, corrosion inhibitors, solvation enhancers, and wetting agents, as known to those of skill in the art. The additive may be, e.g., a carbonate such as ethylene carbonate (EC) or vinylene carbonate (VC), or a polar or aprotic solvent. In some embodiments, these additives are present in the electrolyte solution in the electrolyte solution in an amount of between 0.01% and 10% by weight, or between 0.01% and 5% by weight.

In some embodiments, the electrochemical cell optionally includes at least one separator (130), each separator positioned at least partially between two of the two or more electrodes. In some embodiments, the separator is a porous polyolefin or glass microfiber separator, a polymer separator that is gellable with the electrolytes, or a ceramic or glass solid electrolyte separator.

In some embodiments, the electrochemical cell optionally includes at least one current collector, which may be any appropriate current collector as understood by those of skill in the art. For example, the current collector may be a metal foil, such as copper, nickel, titanium, or platinum.

The disclosed solvent/salt combination significantly reduces irreversible losses, limits interphasial impedance growth and enables the most challenging cell chemistries with high efficiency and long cycle life. The advanced battery chemistries employing cathode materials of either very high voltage or very high capacities, or anode materials with high capacities can benefit from the presence of this unique new combination of solvent and salt chemistry. Such advanced battery electrode chemistries include, but are not limited to, Li-ion batteries of very high voltages (>4.5 V) such as LiNi$_{0.5}$Mn$_{1.5}$O$_2$ (LNMO), LiCoPO4 (LCP) or LiNiPO4, Li[Ni$_x$Mn$_y$Co$_z$]O$_2$ (NMC, including 111, 442, 532, 622, 811, etc.) and cathode or anode materials that can provide extremely high capacities while undergoing extremely dynamic phase changes, such as conversion-reaction-type cathode materials based on metal oxides or halides, Metal/O$_2$ chemistries, sulfur-based cathode materials, as well as graphitic anode materials or those based on an alloy-type mechanism such as silicon or tin.

Having described the invention, the following examples are given to illustrate specific applications of the invention including the best mode now known to perform the invention. They are intended to provide those of ordinary skills in the art with a complete disclosure and description of how to make and use the novel solvents and additives of this invention. These specific examples are not intended to limit the scope of the invention described in this application.

EXAMPLE 1

Preparation of Novel Electrolyte Solutions

This example summarizes a general procedure for the preparation of electrolyte solutions comprising the novel solvent/salt combination. Both the concentration of the active cation salts and the relative ratios between the solvents or salts can be varied according to needs.

The electrolyte solutions were prepared in an Ar-filled glove box with rigorous exclusion of H$_2$O and O$_2$ (both <0.1 ppm) to have the following composition: one perfluoroalkylsulfonyl imide salt of the battery's active cation or a mixture of multiple of these salts, and a solvent system that either comprises a neat solvent or solvent mixture of members of the sulfone family (cyclic and/or aliphatic). These electrolyte formulations may contain additives (<5 wt %) or co-salts (50% of total concentration or less) depending on the formulation.

The perfluoroalkylsulfonyl imide salts selected may be of the form $Li[N(SO_2C_nF_{2n+1})(SO_2C_mF_{2m+1})]^-$ where $m+n \geq 1$ and include, but are not limited to, lithium bis(trifluoromethane)sulfonimide (LiTFSI), lithium bis(perfluoroethanesulfonyl)imide (LiBETI), or their mixtures at varying ratios, or their alkali metal ion or alkali earth metal ion analogs (e.g., sodium bis(fluorosulfonyl)imide (NaFSI)), or multivalent metal ion (e.g., zinc bis(trifluoromethane)sulfonimide ($Zn(TFSI)_2$).

The electrolyte formulation consists of the above sulfonylimide salts or their mixtures at varying ratios dissolved in different sulfone solvents at different concentrations, which is preferably above 0.1M (higher for Li salts). In some embodiments, the concentration are above 2M.

The electrolyte solvents, mixed with or without water, were selected from the sulfone family and include, but are not limited to, tetramethylene sulfone (sulfolane), ethylmethyl sulfone (EMS), dimethylsulfone, trimethylene sulfone, 1-methyltrimethylene sulfone (MTS), ethyl-sec-butyl sulfone (EsBS), ethyl-iso-butyl sulfone (EiBS), ethyl-isopropyl sulfone (EiPS), and also 3,3,3-trifluoropropylmethyl sulfone (FPMS).

Typically, the solvent or solvent mixtures with or without the additives were weighed and mixed according to specific ratios, then the lithium or zinc salt or mixture of lithium salts were weighed and dissolved in the above solvent or solvent mixtures to achieve the desired concentration.

With purpose of illustration only, Table 3 lists some examples of electrolyte solutions prepared and tested. It should be noted that the compositions disclosed in Table 3 may or may not be the optimum compositions for the electrochemical devices in which they are intended to be used, and they are not intended to limit the scope of the present invention.

Table 3. Select Electrolyte Solutions
LiTFSI/Sulfolane (1M)
$Zn(TFSI)_2/H_2O$ (1/15.87 by mol)
$Zn(TFSI)_2/H_2O$/Sulfolane (1/15.06/0.53 by mol)
$Zn(TFSI)_2/H_2O$/Sulfolane (1/13.11/1.78 by mol)
$Zn(TFSI)_2/H_2O$/Sulfolane (1/10.62/3.38 by mol)
$Zn(TFSI)_2/H_2O$/Sulfolane (1/7.46/5.54 by mol)
$Zn(TFSI)_2/H_2O$/Sulfolane (1/2.95/8.46 by mol)

EXAMPLE 2

Fabrication and Galvanostatic Testing of a Zn/Zn Symmetric Cell with the Proposed Electrolyte This example summarizes the general procedure of the assembly of a Zn/Zn symmetric cell. A piece of glass fiber separator was sandwiched between a Zn foil anode and a piece of Zn foil cathode. The Zn/Zn cell was then activated by soaking the separator with the electrolyte solutions as prepared in Example 1 and sealed with an appropriate means.

The fabricated symmetric cells were subject to galvanostatic cycling. In this test, symmetric cells were cycled with current and areal capacity of 0.5 mA/cm$^2$, 0.5 mAh/cm$^2$ and 1 mA/cm$^2$, 1 mAh/cm$^2$, respectively, at 25° C.

Figure 2A:
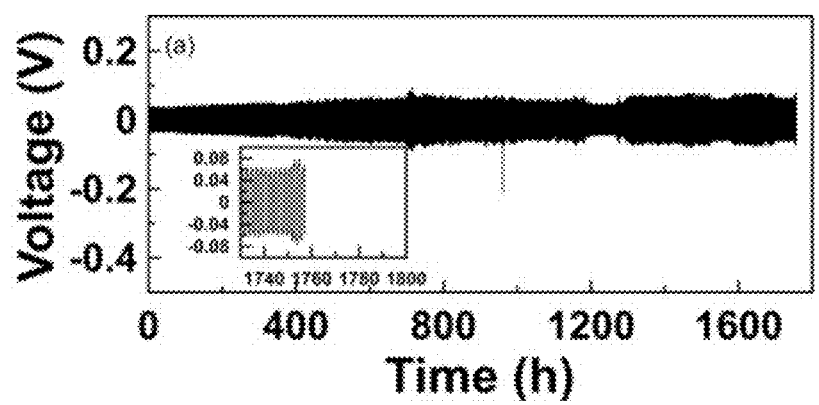
FIG. 2A is a graph depicting voltage over time for a Zn/Zn symmetric cell cycling with Zn(TFSI)$_2$/H$_2$O/Sulfolane (1/10.62/3.38 by mol) at room temp (~25 ° C.) with 0.5 mA/cm$^2$, 0.5 mAh/cm$^2$.
Figure 2B:
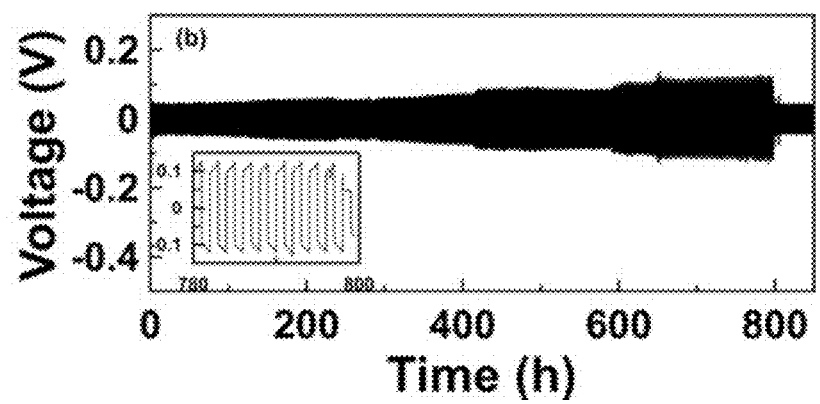
FIG. 2B is a graph depicting voltage over time for a Zn/Zn symmetric cell cycling with Zn(TFSI)$_2$/H$_2$O/Sulfolane (1/10.62/3.38 by mol) at room temperature (~25 ° C.) with 1 mA/cm$^2$, 1 mAh/cm$^2$.

As example for the purpose of illustration, FIGS. 2A and 2B show the voltage over time for a Zn/Zn symmetric cell cycling with $Zn(TFSI)_2/H_2O$/Sulfolane (1/10.62/3.38 by mol) at room temp (~25° C.) with 0.5 mA/cm$^2$, 0.5 mAh/cm$^2$ (FIG. 2A) and 1 mA/cm$^2$, 1 mAh/cm$^2$ (FIG. 2B).

EXAMPLE 3

Fabrication and Galvanostatic Testing of a Cu/Zn Cell with the Proposed Electrolyte This example summarizes the general procedure of the assembly of a Cu/Zn cell. Here, a piece of glass fiber separator was sandwiched between a Zn foil anode and a piece of Cu foil cathode. The Cu/Zn cell was then activated by soaking the separator with the electrolyte solutions as prepared in Example 1 and sealed with appropriate means.

The fabricated cells were subject to galvanostatic testing on Zn stripping/plating Coulombic efficiency (CE). In this test, Cu was conditioned by plating (0.5 mA/cm$^2$, 5 mAh/cm$^2$) and stripping Zn (0.5 V) during the first cycle. Then a Zn reservoir with a capacity of 5 mAh/cm$^2$ ($Q_t$) was built on the substrate metal by using the same current density used for the following cycling. 0.5 mA/cm$^2$ was used for stripping and plating Zn during the following 9 cycles. A capacity of 1mAh/cm$^2$ ($Q_c$) Zn was plated or stripped in each cycle. In the final step, a capacity ($Q_s$) was observed when plated Zn was stripped by charging to 0.5 V. The average CE is calculated based on the following Equation 1:

$$CE = \frac{9Qc + Qs}{9Qc + Qt} \quad (1)$$

Figure 3:
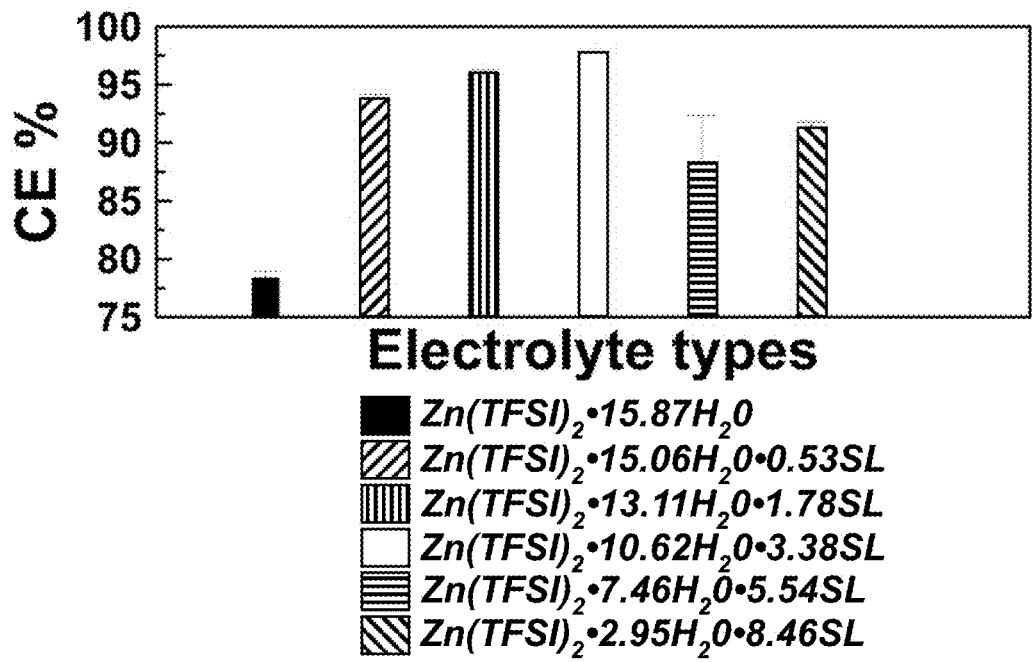
FIG. 3 is a graph of summarized Zn stripping/plating CE results obtained from Cu/Zn cells with selected electrolytes at room temperature (~25 ° C.).

As example for the purpose of illustration, the summarized CE results of Cu/Zn cells in the selected electrolyte were shown in FIG. 3.

EXAMPLE 4

Fabrication and Galvanostatic Testing of a $Na_2V_6O_{16} \cdot 1.63 H_2O$ (HNVO)/Zn Full Cell with the Proposed Electrolyte This example summarizes the general procedure of the assembly of a HNVO/Zn full cell. Here, a piece of glass fiber separator was sandwiched between a Zn foil anode and a piece of HNVO cathode with Ti foil as a current collector. The HNVO/Zn cell was then activated by soaking the separator with the electrolyte solutions as prepared in Example 1 and sealed with appropriate means.

The fabricated cells were subject to galvanostatic cycling. In this test, HNVO/Zn cells were cycled with current of 300 mA/g (mass of HNVO) between 0.2 and 1.6 V at 30° C.

Figure 4:
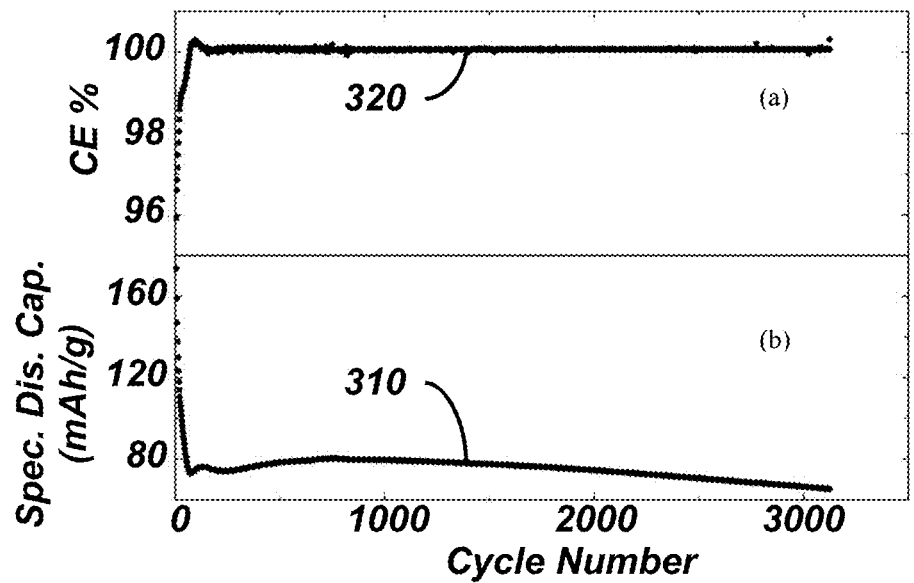
FIG. 4 is a graph illustrating the specific discharge capacity (310) and its corresponding CE (320) vs. cycle number of a HNVO/Zn full cell with Zn(TFSI)$_2$/H$_2$O/Sulfolane (1/10.62/3.38 by mol) tested using 300 mA/g between 0.2 and 1.6 V at 30° C.

As example for the purpose of illustration, the galvanostatic cycling results of HNVO/Zn cells in the selected electrolyte were shown in FIG. 4.

Those skilled in the art will recognize or be able to ascertain using no more than routine experimentation, many equivalents to the specific embodiments of the invention described herein. Such equivalents are intended to be encompassed by the following claims.

What is claimed is:
1. An electrochemical cell comprising:
two or more electrodes operably connected to an electrolyte solution, the electrolyte solution containing:
an aliphatic or cyclic sulfone; and
a metal perfluoroalkylsulfonylimide salt, wherein the metal perfluoroalkylsulfonylimide salt has a total molar mass >200 g/mol and is present in the electrolyte solution at a concentration of between 0.1 M and 10 M.

2. The electrochemical cell according to claim 1, wherein the aliphatic or cyclic sulfone is tetramethylene sulfone (sulfolane), trimethylene sulfone (TriMS), 1-methyltrimethylene sulfone (MTS), ethylmethyl sulfone (EMS), ethyl-sec-butyl sulfone (EsBS), ethyl-iso-butyl sulfone (EiBS), ethyl-iso-propyl sulfone (EiPS), trifluoropropylmethyl sulfone (FPMS), dimethylsulfone, methanesulfonyl fluoride, or a combination thereof.

3. The electrochemical cell according to claim 2, wherein the electrolyte solution further comprises water.

4. The electrochemical cell according to claim 1, wherein the metal perfluoroalkylsulfonylimide salt comprises Li, Na, Zn, Mg, Ca, or Al.

5. The electrochemical cell according to claim 1, wherein the metal perfluoroalkylsulfonylimide salt is lithium bis(trifluoromethane)sulfonimide (LiTFSI), lithium bis(perfluoroethanesulfonyl)imide (LiBETI), sodium bis(fluorosulfonyl)imide (NaFSI), magnesium bis(trifluoromethane) sulfonimide ($Mg(TFSI)_2$), zinc bis(trifluoromethane) sulfonimide ($Zn(TFSI)_2$), or combinations thereof.

6. The electrochemical cell according to claim 1, further comprising a separator positioned at least partially between the electrodes.

7. The electrochemical cell according to claim 6, wherein the separator is a porous polyolefin or glass microfiber separator, a polymer separator that is gellable with the electrolytes, or a ceramic or glass solid electrolyte separator.

8. The electrochemical cell according to claim 1, further comprising an additive which is present in the electrolyte solution in an amount of between 0.01% and 10% by weight.

9. The electrochemical cell according to claim 1, wherein the electrochemical cell is configured to output at a voltage greater than 3.0V.

10. The electrochemical cell according to claim 1, wherein the electrochemical cell is a battery, a capacitor, a supercapacitor, or an electrolysis cell.

* * * * *